United States Patent
Birlem

(10) Patent No.: US 7,324,201 B2
(45) Date of Patent: *Jan. 29, 2008

(54) YARN SENSOR

(75) Inventor: Olav Birlem, Schwalmtal (DE)

(73) Assignee: Oerlikon Textile GmbH & Co. KG, Monchengladbach (DE)

( * ) Notice: Subject to any disclaimer, the term of this patent is extended or adjusted under 35 U.S.C. 154(b) by 83 days.

This patent is subject to a terminal disclaimer.

(21) Appl. No.: 11/245,411

(22) Filed: Oct. 6, 2005

(65) Prior Publication Data

US 2006/0098200 A1    May 11, 2006

(30) Foreign Application Priority Data

Nov. 6, 2004    (DE) .................. 10 2004 053 735

(51) Int. Cl.
*G01N 21/84* (2006.01)

(52) U.S. Cl. .................. 356/429; 356/430

(58) Field of Classification Search ........... 356/429, 356/430, 431, 237.1, 238.2, 238.3, 239.3, 356/242.1; 73/160
See application file for complete search history.

(56) References Cited

U.S. PATENT DOCUMENTS

| | | | | |
|---|---|---|---|---|
| 2,327,257 A | * | 8/1943 | Gary et al. ............... | 356/394 |
| 3,461,299 A | * | 8/1969 | Felix ...................... | 250/559.12 |
| 3,712,743 A | * | 1/1973 | Harris et al. .............. | 356/430 |
| 4,739,176 A | * | 4/1988 | Allen et al. ............ | 250/559.45 |
| 4,815,833 A | * | 3/1989 | Zobel et al. .............. | 359/726 |
| 4,948,260 A | * | 8/1990 | Felix et al. .............. | 356/429 |
| 5,054,317 A | | 10/1991 | Laubscher ............... | 73/160 |
| 5,377,967 A | | 1/1995 | Eberle .................... | 271/11 |
| 5,414,520 A | | 5/1995 | Joss et al. ............... | 356/430 |
| 5,421,529 A | | 6/1995 | Hans ..................... | 242/36 |
| 5,499,794 A | | 3/1996 | Aeppli .................. | 250/559.45 |
| 5,724,150 A | * | 3/1998 | Schaede et al. ............ | 356/429 |

(Continued)

FOREIGN PATENT DOCUMENTS

DE    101 50 581 A1    4/2003

(Continued)

OTHER PUBLICATIONS

Sparavigna, A. et al. "Beyond capacitive systems with optical measurements for yarn evenness evaluation", Mechatronics 14 (2004) pp. 1183-1196.*

*Primary Examiner*—Tarifur Chowdhury
*Assistant Examiner*—Tara S Pajoohi
(74) *Attorney, Agent, or Firm*—Kennedy Covington Lobdell & Hickman, LLP

(57) ABSTRACT

A yarn sensor for textile spinning and bobbin-winding machines for optically scanning a longitudinally traveling yarn (3) within a measurement gap (19), particularly for detecting extraneous fibers, includes a light source (20), a first receiver (23) for directly transmitted light, two further receivers (21, 22) for light reflected from the yarn (3), and light transmitting elements (24, 25, 26, 27) between the light source (20), measurement gap (19) and receivers (21, 22, 23). In the absence of the yarn (3), the receivers (21, 22) detect projected images of the opposite wall (62) of the measurement gap (19), located essentially outside both sides of the area of the wall (62) of the measurement gap (19) illuminated by the direct radiation of the light-emitting diode (20). As a result, parasitic signals are suppressed, improving the detection of extraneous fibers.

13 Claims, 4 Drawing Sheets

U.S. PATENT DOCUMENTS

| | | | |
|---|---|---|---|
| 5,768,938 A * | 6/1998 | Schilling et al. | 73/160 |
| 5,867,309 A * | 2/1999 | Spink et al. | 359/377 |
| 6,175,408 B1 | 1/2001 | Henze et al. | 356/238.3 |
| 6,499,345 B1 | 12/2002 | Bucher et al. | 73/160 |
| 6,744,498 B2 | 6/2004 | Henze et al. | 356/238.3 |
| 2003/0070481 A1 | 4/2003 | Birlem | 73/160 |
| 2004/0032205 A1* | 2/2004 | Hack et al. | 313/504 |
| 2005/0083521 A1* | 4/2005 | Kamerman | 356/301 |
| 2006/0098201 A1* | 5/2006 | Birlem | 356/429 |

FOREIGN PATENT DOCUMENTS

| | | |
|---|---|---|
| EP | 0 197 763 B1 | 10/1986 |
| EP | 0 213 587 B1 | 3/1987 |
| EP | 0 401 600 A2 | 12/1990 |
| EP | 0 553 455 B1 | 8/1993 |
| EP | 0 571 591 B1 | 12/1993 |
| EP | 0 572 592 B1 | 12/1993 |
| EP | 0 761 585 A1 | 3/1997 |
| EP | 1 018 645 A1 | 7/2000 |
| EP | 1 100 742 B1 | 5/2001 |
| EP | 1 143 236 A2 | 10/2001 |
| WO | WO 93/19359 | 9/1993 |

* cited by examiner

YARN SENSOR

CROSS-REFERENCES TO RELATED APPLICATIONS

This application claims the benefit of German patent application 102004053735.6 filed Nov. 6, 2004, herein incorporated by reference.

BACKGROUND OF THE INVENTION

The present invention relates to a yarn sensor for optically scanning a yarn moving in its longitudinal direction in a measurement gap, particularly for detecting extraneous fibers.

European Patent Disclosure EP 1 018 645 B1 describes a yarn sensor for detecting extraneous material in the yarn, in which a white-light light-emitting diode serves as the light source. A white-light light-emitting diode makes it possible to embody the yarn sensor compactly. The broad color spectrum of the white-light LED (The abbreviation "LED" is commonplace for light-emitting diodes) prevents the occurrence of an unequal color sensitivity of the yarn sensor, or the failure to detect some colors. The detected measured values are examined for characteristics that can indicate that extraneous substances, such as extraneous fibers, are present in the yarn.

European Patent Disclosure EP 0 761 585 A1 describes a generic type of yarn sensor that can likewise serve not only to determine the yarn diameter, but also to detect extraneous material in the yarn, such as extraneous fibers or contaminants. In yarn sensors, the deposition of dirt, such as dust and fiber particles, on surfaces of the measurement gap that are unprotected against becoming soiled, is unavoidable. It is true that a certain self-cleaning effect occurs in the measurement gap, brought about by the yarn moving through the measurement gap. However, this known self-cleaning effect cannot prevent surfaces in the measurement gap, on which light from the light source shines, from becoming at least temporarily soiled. For instance, if the protective plate between the yarn and the receiver for directly transmitted light becomes soiled, not only is the quantity of light arriving at this receiver reduced, but the dirt particles also reflect the arriving light projected by the light source. The light reflected by the yarn, because of the small surface area of the yarn, represents a relatively small signal source. The yarn signal converted into current varies in the nanoampere range. Compared to the small irradiated surface of the yarn, the relatively large, dirty surface of the measurement gap, because of its length, represents a not inconsiderable source of reflection signals. The interfering radiation, which adulterates the result of the measurement, is also called a parasitic signal. Because of the low intensity of the yarn signal, a high amplification of the signal converted from the incident light at the yarn takes place, but high amplification of the parasitic signals occurs as well. This leads to an impermissibly small useful signal, in proportion to the total signal.

Both the yarn sensor of European Patent Publication EP 0 018 645 B1 and the yarn sensor of European Patent Publication EP 761 585 A1 are incapable of overcoming this disadvantage.

SUMMARY OF THE INVENTION

It is accordingly an object of the present invention to improve the known yarn sensors such as those of European Patent Publications EP 0 018 645 B1 and EP 761 585 A1.

Briefly summarized, the present invention provides a yarn sensor for optically scanning a yarn traveling in its lengthwise direction through a measurement gap, basically comprising a light source for projecting a beam of light across the measurement gap, a first receiver for directly transmitted light, a second receiver for light reflected from the yarn, a third receiver for light reflected from the yarn, and elements for transmitting the light between the light source, measurement gap and receivers. In accordance with the invention, the light transmitting elements comprise a first light-transmitting element disposed between the light source and the measurement gap and including a diaphragm and a lens, downstream of the light source in the direction of light projection, and arranged such that the diaphragm is projected at least approximately into infinity. Second and third light-transmitting elements are also respectively disposed between the measurement gap and the second and third reflected light receivers. Each of the second and third light-transmitting elements comprise a lens disposed upstream in the projected direction of the light reflected from the yarn such that, in the absence of the yarn, projected images on an opposing surface of the measurement gap are detectable by the second and third receivers essentially outside both opposite sides of a projected image of the light source across the measurement gap.

The described embodiment of the yarn sensor according to the present invention has the effect that essentially only light from the light source that is reflected by the yarn reaches the two receivers for reflected light. Interference and adulteration from parasitic signals can be reduced markedly. The measurement sensitivity of the yarn sensor can be adjusted more sensitively.

The light source is advantageously a light-emitting diode. Light-emitting diodes require only little space and are therefore especially well suited to use at work stations of spinning or bobbin winding machines, where only very limited space is available. The light-emitting diode is preferably embodied as a white-light LED. The color spectrum of the white-light LED offers a variety of possibilities in color recognition. The use of additional light-emitting diodes with light in other colors can be economically dispensed with, and the required space can be kept small. Since a white-light LED serving as the sole light source emits light in all the colors needed, a constant sensitivity of the yarn sensor to different colors is made possible. A single white-light LED comes substantially closer to the model of a point light source than an array of two or more light-emitting diodes.

The yarn sensor may further comprise a diffusor disposed between the light source and the diaphragm upstream of the diaphragm and the diffusor may be, for example, a film for generating divergent beams of light from beam of light of the light source. In such manner, a uniform illumination of the measurement gap is attained so as to maximally avert an adulterating influence on the sensor signals generated, which influence is dependent on the position of the yarn in the measurement gap.

The lens of the first light transmitting element may have its light entrance side arranged to homogeneously distribute the luminous intensity of the light beam from the light source in the direction of the optical axis of the lens and its exit side arranged to project the light beam arriving from the entrance side essentially parallel to the optical axis of the lens. In this manner, it becomes possible for the yarn to move in a light that comprises very homogeneous, quasi-parallel radiation. Scattered light that strikes the measurement gap surface outside the intentionally irradiated region is minimized or suppressed entirely. The measurement signals are not attenuated.

If the elements for transmitting the light are separated from the measurement gap by windows, which may include glass plates, protection of the elements for transmitting the light is accomplished.

A second diaphragm with a rectangular aperture may be disposed between the lens of the first light transmitting element and the yarn, which limits the beam of light aimed at the yarn in such a way that only areas that cause no reflections that lead to parasitic signals are illuminated.

Each of the second and third light transmitting elements may further comprise a diaphragm, optionally including a window, disposed between the yarn and the lens in path of the light reflected by the yarn. The disposition of such a diaphragm in the beam path of the light reflected by the yarn to the receiver serves to avoid unwanted reflections that generate parasitic signals. The homogeneity of the light in the beam of light aimed at the receiver can be improved.

In the measurement field, measurement signals occur that are not useful signals and that make the evaluation more difficult. The embodiment of the yarn sensor according to the invention causes the magnitude of the useful signal not to be dependent on the position of the yarn in the measurement field. The proportion of the useful signal in the total measurement signal becomes greater because of the elements used and disposed according to the invention. Therefore, even extraneous fibers that were not detectable by methods and apparatuses of the prior art can be reliably detected. In one possible embodiment, a signal processing device may be arranged to detect and evaluate signal incursions and signal exaggerations, which for instance enables polypropylene (PP) fibers to be detected, as their signal exaggeration is as a rule less than the signal incursion caused for instance by colored extraneous fibers. This makes a targeted removal of the PP fibers from the yarn possible and thus avoids the occurrence of inadequate quality or even rejection when the yarn is subjected to a dyeing process.

With a yarn sensor according to the present invention, the quality of he measurement outcome for the detection of extraneous fibers is improved.

Further details, features and advantages of the present invention will be described and understood from following specification with reference to the illustrations in the accompanying drawings.

DESCRIPTION OF THE PREFERRED EMBODIMENT

Figure 1:
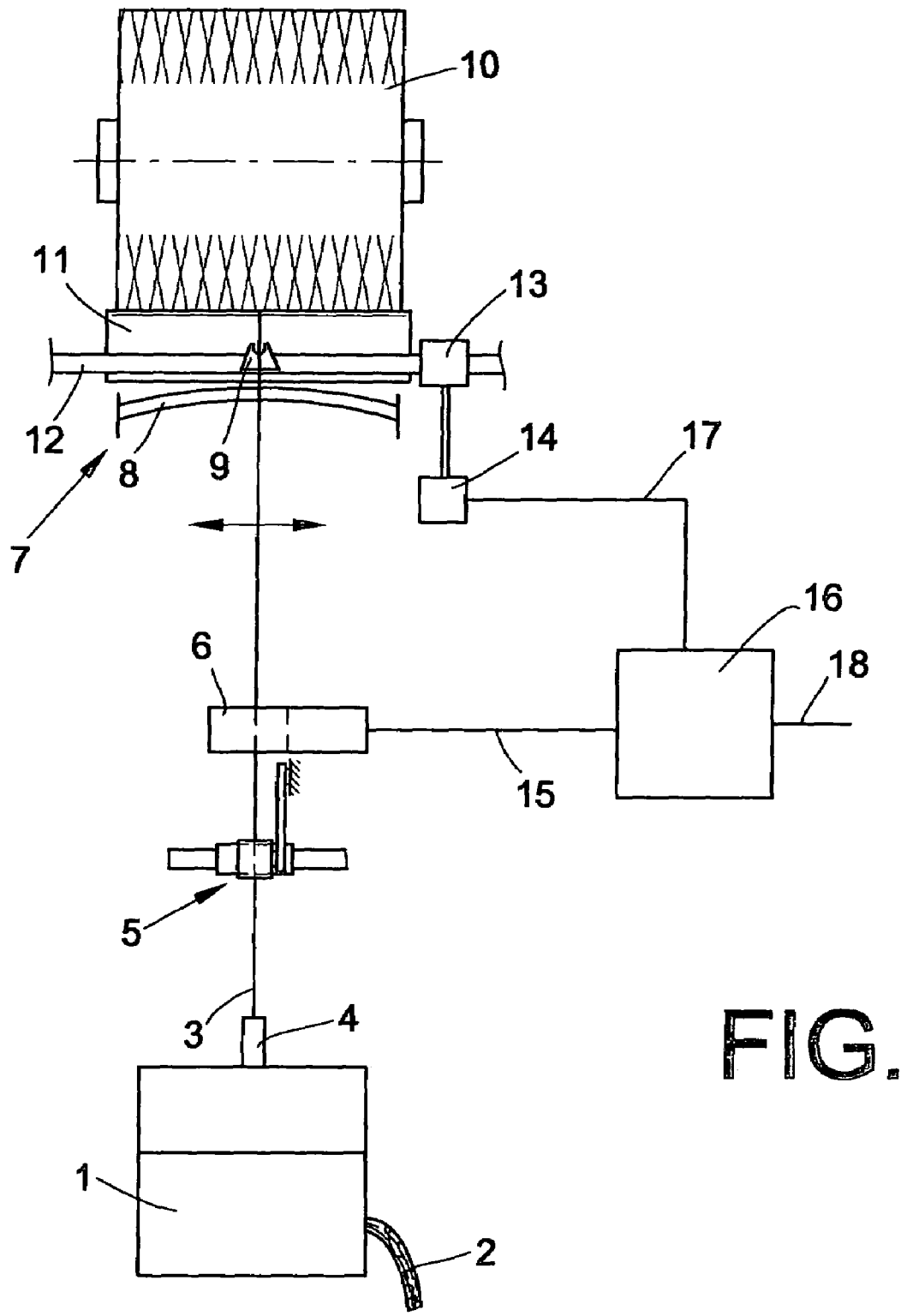
FIG. 1 is a schematic illustration of the basic elements of a yarn spinning station.

Referring now to the accompanying drawings, FIG. 1 shows a spinning box 1 of an open-end spinning machine, to which a sliver 2 is being delivered. The yarn 3 made in the spinning box 1 is withdrawn via the draw-off tube 4 by means of a pair of draw-off rollers 5, passes through a yarn sensor 6, and is directed via a hoop 8 to be wound up, by the reciprocating motion of a yarn guide 9 of a traversing device 7, over a predetermined width into a cross-wound bobbin, also referred to as a cheese 10. The cheese 10 is driven by means of a friction roller 11. The yarn guide 9 is secured to a yarn guide 12, which is moved back and forth by a yarn guide gear 13. The drive of the yarn guide gear 13 is effected by means of a drive device 14. The yarn sensor 6 for monitoring the moving yarn 3 is located above the pair of draw-off rollers 5, in the region of the traversing movement of the yarn 3. In an alternative embodiment, not shown, the yarn sensor 6 may be located upstream, instead of downstream, of the pair of draw-off rollers 5. The yarn sensor 6 communicates via a line 15 with a control unit 16, which receives the signals emitted by the yarn sensor 6. Via a further line 17, the control unit 16 is connected to the drive device 14. The drive device 14 is preferably embodied as an electric motor. Via the line 18, the control unit 16 communicates with further spinning stations, data processing devices, or spinning machines, not shown here.

Figure 2:
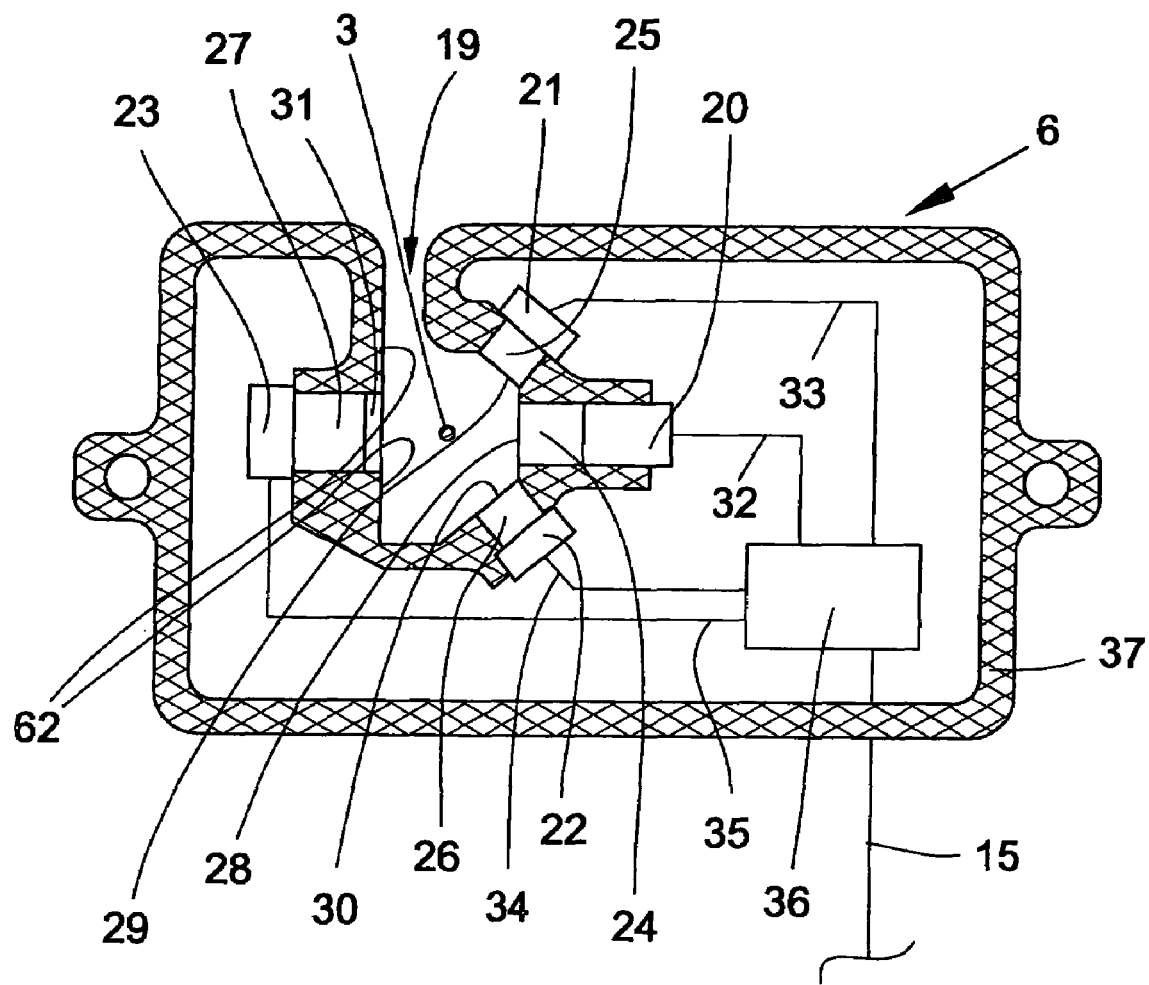
FIG. 2 is a cross-sectional view of a yarn sensor according to the present invention, showing the housing open.

From FIG. 2 depicts the location of individual components of the yarn sensor 6 relative to the measurement gap 19 and the yarn 3. The light source, embodied as a light-emitting diode 20, and photodiodes 21, 22, which serve to receive the light reflected by the yarn 3, are positioned to the right, as viewed in FIG. 2, of the measurement gap 19. A photodiode 23 for receiving the light transmitted directly by the light-emitting diode 20 is positioned to the left of the measurement gap 19, as viewed in FIG. 2. Elements 24, 25, 26, 27 for transmitting the light are disposed between the light-emitting diode 20 and the measurement gap 19, on the one hand, and between the measurement gap 19 and the photodiodes 21, 22, 23 on the other hand. The light transmitting elements 24, 25, 26, 27 are separated from the measurement gap 19 by windows 28, 29, 30, 31. The windows can provide protection of the light transmitting elements 24, 25, 26, 27 against becoming soiled with dust and fluff. The light-emitting diode 20 and the photodiodes 21, 22, 23 each communicate with a signal processing device 36 by means of the lines 32, 33, 34, 35. The signal processing device 36 communicates in turn with the control unit 16 via the line 15, which leads through the housing 37 of the yarn sensor 6 to the outside.

Figure 3:
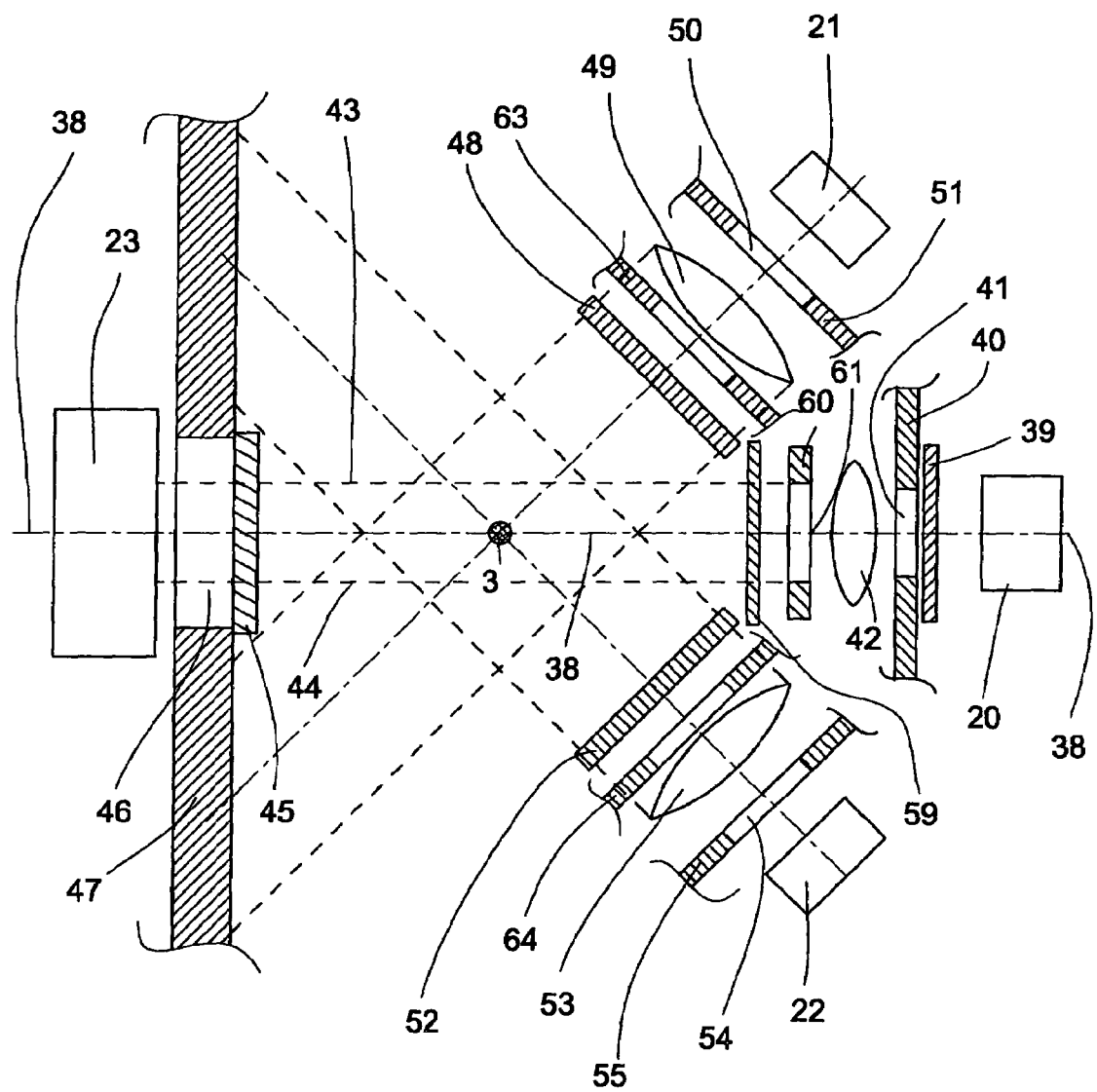
FIG. 3 is an enlarged cross-sectional view of an arrangement of the operative elements of the yarn sensor of FIG. 2.

FIG. 3 shows a more detailed arrangement of the components of the yarn sensor 6, which is suitable for detecting extraneous substances or materials in the yarn 3. As the light source, the light-emitting diode 20 is used, which has approximately the same emission characteristic as a Lambert emitter. The light-emitting diode 20 is embodied as a white-light LED. White-light LEDs emit light with a broad emission spectrum. If a white-light LED is used, it is possible to dispense with using a plurality of light-emitting diodes for emitting different colors or for amplifying the emitted light. The light emitted by the light-emitting diode 20 passes through the light transmitting element 24. The element 24 includes a film 39, a diaphragm 40 with an aperture 41, a lens 42, a diaphragm 60 with a rectangular aperture 61, and a glass plate 59, through which light passes in succession in the direction of the optical axis 38. The aperture 41 of the diaphragm 40 has a width of 1 mm. The film 39 projects divergent beams of light and has the emission characteristic of a Lambert emitter. As the film 39, the film type Oracal 8500, translucent series, made by the company known and doing business as K. Gröner is used, for instance. This film has been used previously for advertising labels, that is, in a field that is completely different from use in a yarn sensor for increasing the measurement accuracy, as in the present invention. Downstream of the lens 42, the individual beams of light. are oriented quasi-parallel to one another in the direction of the optical axis 38 and are distributed homogeneously over the cross section of the total beam of light. The total beam of light is represented by the two dashed lines 43, 44. The film 39 forms a virtual light source, which is projected to infinity. Along the projected pathway of the beam of light between the lens 42 and the image plane of the photodiode 23, the projection of the virtual light source is always present. This projection itself, however, is blurry. This effect is associated with a further homogenizing of the beam of light. The traveling yarn 3 crosses through the course of the total beam of light and is projected in the form of a shadow on the photodiode 23. Between the yarn 3 and the photodiode 23, the total beam of light passes through both the glass plate 45 and the aperture 46 of the diaphragm 47. Some of the light emitted by the light-emitting diode 20 is reflected by the yarn 3. The photodiodes 21, 22 detect some of the reflected light. Between the yarn 3 and the photodiodes 21, 22, a portion of the reflected light passes through each of the light transmitting elements 25, 26. The reflected light transmitting elements 25, 26 each include the associated glass plate 48, 52, the diaphragm 63, 64, the lens 49, 53, and the aperture 50, 54 of the diaphragm 51, 55, respectively. The reflected light transmitting elements 25, 26 are embodied and disposed such that, if the yarn 3 is absent, then by means of the photodiodes 21, 22 projected images of the opposite surfaces, for instance of the diaphragm 40 or of the wall 62 of the measurement gap 19, are detectable. These surfaces are located on both sides, outside the area of the wall 62 of the measurement gap 19 that is illuminated by the direct radiation of the light-emitting diode 20.

Alternatively, the diaphragms 51 and 55 may be omitted. The glass plates 48, 52, 59 may, in a further alternative embodiment, be embodied as diaphragms and have rectangular apertures.

Figure 4:
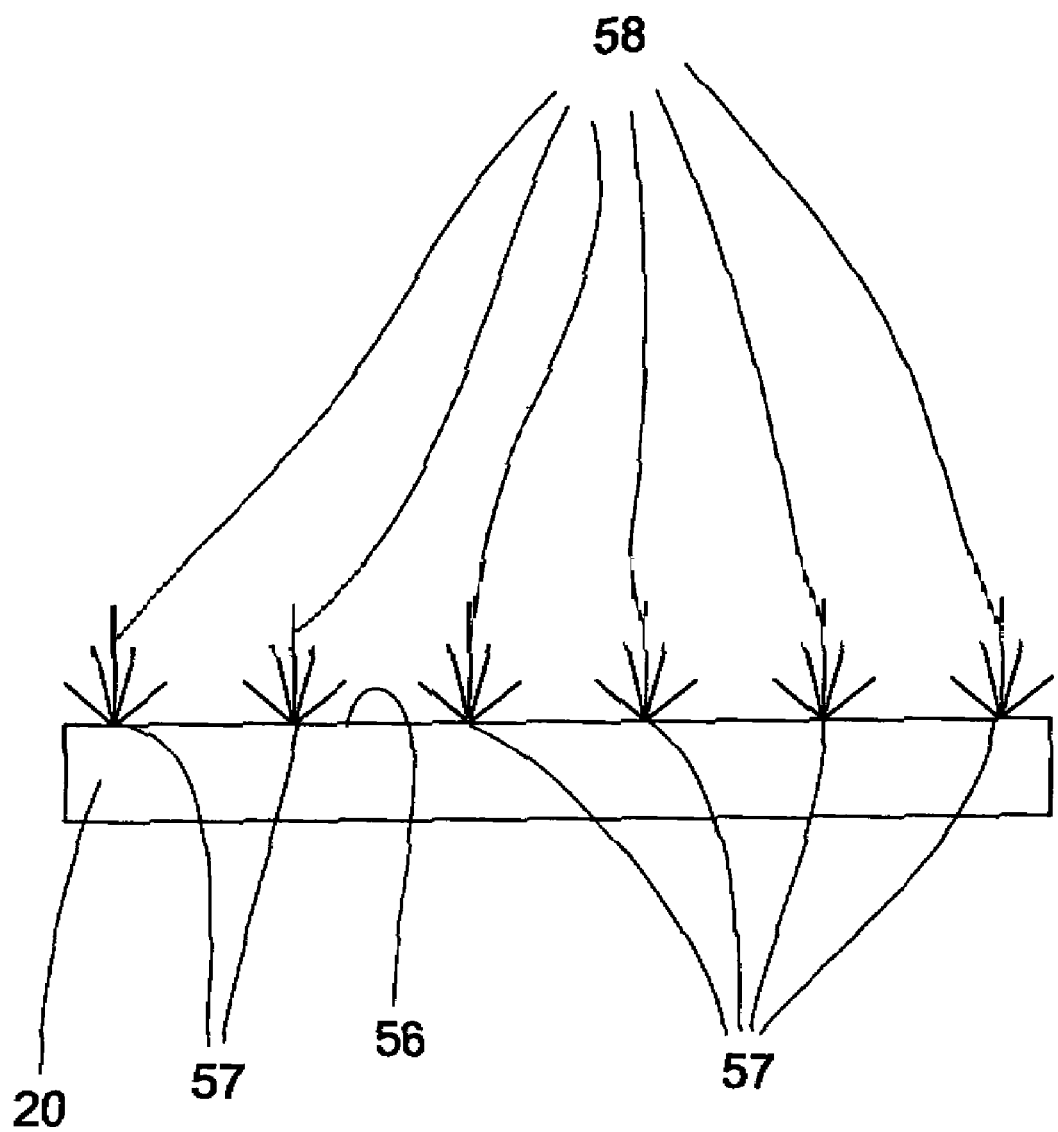
FIG. 4 is schematic illustration of a Lambert area emitter.

FIG. 4 shows the basic illustration of the light-emitting diode 20, whose light-projecting face 56 has the characteristic of a Lambert emitter. From each point 57 of the face 56, a divergent beam 58 is emitted. The light that a Lambert emitter emits can be. converted into a homogeneous light with a quasi-parallel beam path; the homogeneity and the parallelism of the light are better than is the case when conventional so-called point light sources are employed.

The invention is not limited to the exemplary embodiments described. Other embodiments are possible within the scope of the invention, in particular as regards the design of the rotor insert. It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A yarn sensor for optically scanning a yarn traveling in its lengthwise direction through a measurement gap, comprising:
   a light source for projecting a beam of light across the measurement gap,
   a first receiver for directly transmitted light,
   a second receiver for light reflected from the yarn,
   a third receiver for light reflected from the yarn, and
   elements for transmitting the light between the light source, measurement gap and receivers,
   the light transmitting elements comprising:
      a first light-transmitting element disposed between the light source and the measurement gap and including a diaphragm and a lens, downstream of the light source in the direction of light projection, and arranged such that the diaphragm is projected at least approximately into infinity, and
      second and third light-transmitting elements respectively disposed between the measurement gap and the second and third reflected light receivers,
         each of the second and third light-transmitting elements comprising a lens disposed upstream in the projected direction of the light reflected from the yarn such that, in the absence of the yarn, projected images on an opposing surface of the measurement gap are detectable by the second and third receivers essentially outside both opposite sides of a projected image of the light source across the measurement gap.

2. The yarn sensor of claim 1, wherein the light source is a light-emitting diode having an emission characteristic of a Lambert emitter.

3. The yarn sensor of claim 2, characterized in that the light-emitting diode is a white light LED.

4. The yarn sensor of claim 1, wherein a diffusor is disposed between the light source and the diaphragm upstream of the diaphragm.

5. The yarn sensor of claim 4, characterized in that the diffusor is a film for generating divergent beams of light from beam of light of the light source.

6. The yarn sensor of claim 1, wherein the lens of the first light transmitting element comprises a light entrance side arranged to homogeneously distribute the luminous intensity the light beam from the light source in the direction of the optical axis of the lens and comprises an exit side arranged to project the light beam arriving from the entrance side essentially parallel to the optical axis of the lens.

7. The yarn sensor of claim 1, wherein the light transmitting elements are separated from the measurement gap by windows.

8. The yarn sensor of claim 1, wherein a second diaphragm with a rectangular aperture is disposed between the lens of the first light transmitting element and the yarn.

9. The yarn sensor of claim 1, wherein each of the second and third light transmitting elements comprises a diaphragm disposed between the yarn and the lens in path of the light reflected by the yarn.

10. The yarn sensor of claim 9, wherein the diaphragm of each of the second and third light transmitting elements is embodied by a glass plate.

11. The yarn sensor of claim 1, wherein a signal processing device is arranged to detect and evaluate signal interferences.

12. A yarn sensor for optically scanning a yarn traveling in its lengthwise direction through a measurement gap, comprising:

a light source for projecting a beam of light across the measurement gap, wherein the light source is a light-emitting diode having an emission characteristic of a Lambert emitter,
a first receiver for directly transmitted light,
a second receiver for light reflected from the yarn,
a third receiver for light reflected from the yarn, and
elements for transmitting the light between the light source, measurement gap and receivers,
the light transmitting elements comprising:
  a first light-transmitting element disposed between the light source and the measurement gap and including a diaphragm and a lens, downstream of the light source in the direction of light projection, and arranged such that the diaphragm is projected at least approximately into infinity, and
  second and third light-transmitting elements respectively disposed between the measurement gap and the second and third reflected light receivers,
  each of the second and third light-transmitting elements comprising a lens disposed upstream in the projected direction of the light reflected from the yarn such that, in the absence of the yarn, projected images on an opposing surface of the measurement gap are detectable by the second and third receivers essentially outside both opposite sides of a projected image of the light source across the measurement gap.

13. The yarn sensor of claim 12, characterized in that the light-emitting diode is a white light LED.

* * * * *